United States Patent [19]
Jaynes et al.

[11] Patent Number: 6,001,805
[45] Date of Patent: Dec. 14, 1999

[54] METHOD OF ENHANCING WOUND HEALING BY STIMULATING FIBROBLAST AND KERATINOCYTE GROWTH IN VIVO, UTILIZING AMPHIPATHIC PEPTIDES

[75] Inventors: Jesse M. Jaynes, Raleigh; Gordon R. Julian, Cary, both of N.C.

[73] Assignee: Demegen, Inc., Pittsburgh, Pa.

[21] Appl. No.: 08/689,489

[22] Filed: Aug. 12, 1996

Related U.S. Application Data

[63] Continuation of application No. 08/231,730, Apr. 20, 1994, Pat. No. 5,561,107, which is a continuation-in-part of application No. 08/225,476, Apr. 8, 1994, abandoned, which is a continuation-in-part of application No. 08/039,620, Jun. 4, 1993, abandoned, and a continuation-in-part of application No. 08/148,889, Nov. 8, 1993, abandoned, and a continuation-in-part of application No. 08/148,491, Nov. 8, 1993, abandoned.

[51] Int. Cl.⁶ ............................. A01N 1/02; A61K 38/10; A61K 38/16; C12N 5/06
[52] U.S. Cl. ............................. 514/12; 435/1.1; 435/371; 435/405; 514/13; 514/14
[58] Field of Search .................................. 530/324, 325, 530/326, 327, 345; 514/12, 13, 14, 21; 930/290; 435/1.1, 363, 366, 371, 395, 405

[56] References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,810,777 | 3/1989 | Zasloff | 530/326 |
| 5,070,188 | 12/1991 | Njieha et al. | 530/399 |
| 5,294,605 | 3/1994 | Houghten et al. | 514/13 |
| 5,411,942 | 5/1995 | Widmer et al. | 514/11 |
| 5,561,107 | 10/1996 | Jaynes et al. | 514/12 |
| 5,717,064 | 2/1998 | Julian et al. | 530/324 |
| 5,744,445 | 4/1998 | Jaynes et al. | 514/12 |
| 5,773,413 | 6/1998 | Jaynes et al. | 514/12 |

OTHER PUBLICATIONS

Biochemistry, vol. 7, No. 6, Issued Jun. 1968, Means et al, "Reductive Alkylation of Amino Groups in Proteins", pp. 2192–2201.

J. Biol. Chem., vol. 243, No. 23, Issued Dec. 10, 1968, Takahashi, "The Reaction of Phenylglyoxal with Arginine . . . ", pp. 6171–6179.

Jaynes, J.M. et al., "In Vitro Cytocidal Effect of Lytic Peptides On Several Transformed Mammalian Cell Lines," *Peptide Research*, 2:157–160 (1989).

Jaynes, J.M., "Lytic Peptides Portend an Innovative Age in the Management and Treatment of Human Disease," *Drug News and Perspectives*, 3:69–78 (1990).

Akerfeldt, K.S. et al., "Synthetic Peptides as Models for Ion Channel Proteins," *Acc. Chem. Res.*, 26:191–197 (1993).

Reed, W.A. et al., "Enhanced In Vitro Growth of Murine Fibroblast Cells and Preimplantation Embryos Cultured in Medium Supplemented With an Amphipathic Peptide," *Molecular Reproduction and Development*, 31:106–113 (1992).

Arrowood, M.J. et al., "Hemolytic Properties of Lytic Peptides Active Against the Sporozites of *Cryptosporidium Parvum*," *J. Protozool*, 38:161s–163s (1991).

Jaynes, J.M. et al., "In Vitro Cytocidal Effect of Novel Lytic Peptides on *Plasmodium Falciparum* and *Trypanosoma Cruzi*," *Faseb J.*, 2:2878–2883 (1988).

Graham, M.L. et al., "Cytotoxic Effect of Amphipathic Cationic Lytic Peptides on Human and Murine Cancer Cell Lines," *Proceedings of the American Association for Cancer Research* 35:410 (1994).

Moore, A.J. et al., "Preliminary Experimental Anti–Cancer Activity of Cecropin B," *Proceedings of the American Association for Cancer Research*, 35:410 (1994).

*Primary Examiner*—Jeffrey E. Russel
*Attorney, Agent, or Firm*—Rothwell, Figg, Ernst & Kurz

[57] ABSTRACT

A method of treating a wound of a mammalian subject in need of such treatment, to promote healing thereof, comprising administering to the subject, e.g., to the wound locus, a composition comprising a fibroblast and keratinocyte proliferatingly effective amount of an amphipathic peptide, preferably an amphipathic peptide which is antimicrobially effective at such locus. A method is also disclosed of stimulating the accelerated growth of dermal tissue in a tissue culture containing same, comprising applying to the tissue culture a fibroblast and keratinocyte proliferatingly effective amount of an amphipathic peptide, by which the dermal tissue may be grown to produce skin for skin grafting purposes, utilizing a dermal tissue culture containing dermal tissue material of a skin graft recipient of such skin. Novel amphipathic peptides suitable for use in such methods are disclosed.

4 Claims, No Drawings

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 27 amino acids
      (B) TYPE: amino acid
      (C) STRANDEDNESS:
      (D) TOPOLOGY: linear (ii) MOLECULE TYPE: peptide (iii) HYPOTHETICAL: NO (xi) SEQUENCE DESCRIPTION: SEQ ID NO:1:

Phe Ala Val Ala Val Lys Ala Val Lys Lys Ala Val Lys Lys Val
1            5                    10                  15

Lys Lys Ala Val Lys Lys Ala Val Lys Lys Lys Lys
                20                  25

(2) INFORMATION FOR SEQ ID NO:2:

(i) SEQUENCE CHARACTERISTICS:

(A) LENGTH: 32 amino acids
         (B) TYPE: amino acid
         (C) STRANDEDNESS:
         (D) TOPOLOGY: linear (ii) MOLECULE TYPE: peptide (iii) HYPOTHETICAL: NO (xi) SEQUENCE DESCRIPTION: SEQ ID NO:2:

Phe Ala Val Ala Val Lys Ala Val Ala Val Lys Ala Val Lys Lys
1               5                   10                  15

Ala Val Lys Lys Val Lys Lys Ala Val Lys Lys Ala Val Lys Lys
                20                  25                  30

Lys Lys (2) INFORMATION FOR SEQ ID NO:3:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:3:

Phe Ala Val Ala Val Lys Ala Val Ala Val Lys Ala Val Ala Val
1               5                   10                  15

Lys Ala Val Lys Lys Ala Val Lys Lys Val Lys Lys Ala Val Lys
                20                  25                  30

Lys Ala Val Lys Lys Lys Lys
                35

(2) INFORMATION FOR SEQ ID NO:4:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:4:

Phe Ala Val Ala Val Lys Ala Val Lys Lys Ala Val Lys Lys Val
1               5                   10                  15

Lys Lys Ala Val Lys Lys Ala Val
                20

(2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:5:

Phe Ala Val Ala Val Lys Ala Val Ala Val Lys Ala Val Lys Lys

```
           1               5                  10                  15
Ala Val Lys Lys Val Lys Lys Ala Val Lys Lys Ala Val
                    20                  25

(2) INFORMATION FOR SEQ ID NO:6:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:6:

Phe Ala Val Ala Val Lys Ala Val Ala Val Lys Ala Val Ala Val
1               5                  10                  15

Lys Ala Val Lys Lys Ala Val Lys Lys Val Lys Lys Ala Val Lys
                    20                  25                  30

Lys Ala Val (2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:7:

Phe Ala Val Gly Leu Arg Ala Ile Lys Arg Ala Leu Lys Lys Leu
1               5                  10                  15

Arg Arg Gly Val Arg Lys Val Ala Lys Arg Lys Arg
                    20                  25

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:8:

Phe Ala Val Gly Leu Arg Ala Ile Lys Arg Ala Leu Lys Lys Leu
1               5                  10                  15

Arg Arg Gly Val Arg Lys Val Ala
                    20

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide
```

(iii) HYPOTHETICAL: NO (xi) SEQUENCE DESCRIPTION: SEQ ID NO:9:

Lys Arg Lys Arg Ala Val Lys Arg Val Gly Arg Arg Leu Lys Lys
1               5                   10                  15

Leu Ala Arg Lys Ile Ala Arg Leu Gly Val Ala Phe
                20                  25

(2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:10:

Ala Val Lys Arg Val Gly Arg Arg Leu Lys Lys Leu Ala Arg Lys
1               5                   10                  15

Ile Ala Arg Leu Gly Val Ala Phe
                20

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:11:

Phe Ala Val Gly Leu Arg Ala Ile Lys Arg Ala Leu Lys Lys Leu
1               5                   10                  15

Arg Arg Gly Val Arg Lys Val Ala Lys Arg Lys Arg Lys Asp Leu
                20                  25                  30

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:12:

Phe Ala Val Gly Leu Arg Ala Ile Lys Arg Ala Leu Lys Lys Leu
1               5                   10                  15

Arg Arg Gly Val Arg Lys Val Ala Lys Asp Leu
                20                  25

(2) INFORMATION FOR SEQ ID NO:13:

(i) SEQUENCE CHARACTERISTICS:
        (A) LENGTH: 30 amino acids
        (B) TYPE: amino acid

```
            (C) STRANDEDNESS:
            (D) TOPOLOGY: linear (ii) MOLECULE TYPE: peptide (iii) HYPOTHETICAL: NO (xi) SEQUENCE DESCRIPTION: SEQ ID NO:13:

Lys Arg Lys Arg Ala Val Lys Arg Val Gly Arg Arg Leu Lys Lys
1               5                  10                  15

Leu Ala Arg Lys Ile Ala Arg Leu Gly Val Ala Phe Lys Asp Leu
                20                  25                  30

(2) INFORMATION FOR SEQ ID NO:14:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (iii) HYPOTHETICAL: NO (xi) SEQUENCE DESCRIPTION: SEQ ID NO:14:

Ala Val Lys Arg Val Gly Arg Arg Leu Lys Lys Leu Ala Arg Lys
1               5                  10                  15

Ile Ala Arg Leu Gly Val Ala Phe Lys Asp Leu
                20                  25

(2) INFORMATION FOR SEQ ID NO:15:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:15:

Lys Lys Lys Lys Phe Val Lys Val Ala Lys Lys Val Lys Lys
1               5                  10                  15

Val Ala Lys Lys Val Ala Lys Val Ala Val Ala Val
                20                  25

(2) INFORMATION FOR SEQ ID NO:16:

(i) SEQUENCE CHARACTERISTICS:
            (A) LENGTH: 32 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:16:

Lys Lys Lys Lys Phe Val Lys Val Ala Lys Lys Val Lys Lys
1               5                  10                  15

Val Ala Lys Lys Val Ala Lys Val Ala Val Ala Lys Val Ala Val
```

```
                        20                  25                  30
Ala Val (2) INFORMATION FOR SEQ ID NO:17:

(i) SEQUENCE CHARACTERISTICS:
          (A) LENGTH: 37 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:17:

Lys Lys Lys Lys Phe Val Lys Lys Val Ala Lys Lys Val Lys Lys
1               5                   10                  15

Val Ala Lys Lys Val Ala Lys Val Ala Lys Val Ala Val
                20                  25                  30

Ala Lys Val Ala Val Ala Val
                35

(2) INFORMATION FOR SEQ ID NO:18:

(i) SEQUENCE CHARACTERISTICS:
          (A) LENGTH: 23 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:18:

Phe Val Lys Lys Val Ala Lys Lys Val Lys Lys Val Ala Lys Lys
1               5                   10                  15

Val Ala Lys Val Ala Val Ala Val
                20

(2) INFORMATION FOR SEQ ID NO:19:

(i) SEQUENCE CHARACTERISTICS:
          (A) LENGTH: 28 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:19:

Phe Val Lys Lys Val Ala Lys Lys Val Lys Lys Val Ala Lys Lys
1               5                   10                  15

Val Ala Lys Val Ala Val Ala Lys Val Ala Val Ala Val
                20                  25

(2) INFORMATION FOR SEQ ID NO:20:

(i) SEQUENCE CHARACTERISTICS:
```

(A) LENGTH: 33 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:20:

Phe Val Lys Lys Val Ala Lys Lys Val Lys Lys Val Ala Lys Lys
1               5                  10                  15

Val Ala Lys Val Ala Val Ala Lys Val Ala Val Ala Lys Val Ala
                20                  25                  30

Val Ala Val (2) INFORMATION FOR SEQ ID NO:21:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:21:

Lys Lys Lys Lys Phe Val Lys Val Ala Lys Val Ala Lys Lys
1               5                  10                  15

Val Ala Lys Val Ala Lys Lys Val Ala Lys Lys Val
                20                  25

(2) INFORMATION FOR SEQ ID NO:22:

(i) SEQUENCE CHARACTERISTICS:
            (A) LENGTH: 32 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:22:

Lys Lys Lys Lys Phe Val Lys Val Ala Lys Val Ala Lys Lys
1               5                  10                  15

Val Ala Lys Val Ala Lys Lys Val Ala Lys Lys Val Ala Lys Lys
20              25                  30                  35

Val Ala (2) INFORMATION FOR SEQ ID NO:23:

(i) SEQUENCE CHARACTERISTICS:
            (A) LENGTH: 37 amino acids
            (B) TYPE: amino acid
            (C) STRANDEDNESS:
            (D) TOPOLOGY: linear (ii) MOLECULE TYPE: peptide

```
        (iii) HYPOTHETICAL: NO (v) FRAGMENT TYPE: linear (xi) SEQUENCE DESCRIPTION: SEQ ID NO:23:

Lys Lys Lys Lys Phe Val Lys Lys Val Ala Lys Val Ala Lys Lys
1               5                   10                  15

Val Ala Lys Val Ala Lys Lys Val Ala Lys Lys Val Ala Lys Lys
                20                  25                  30

Val Ala Lys Val Ala Lys Lys
                35

(2) INFORMATION FOR SEQ ID NO:24:

(i) SEQUENCE CHARACTERISTICS:
             (A) LENGTH: 23 amino acids
             (B) TYPE: amino acid
             (C) STRANDEDNESS:
             (D) TOPOLOGY: linear (ii) MOLECULE TYPE: peptide (iii) HYPOTHETICAL: NO (xi) SEQUENCE DESCRIPTION: SEQ ID NO:24:

Phe Val Lys Lys Val Ala Lys Val Ala Lys Lys Val Ala Lys Val
1               5                   10                  15

Ala Lys Lys Val Ala Lys Lys Val
                20

(2) INFORMATION FOR SEQ ID NO:25:

(i) SEQUENCE CHARACTERISTICS:
             (A) LENGTH: 28 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:25:

Phe Val Lys Lys Val Ala Lys Val Ala Lys Lys Val Ala Lys Val
1               5                   10                  15

Ala Lys Lys Val Ala Lys Lys Val Ala Lys Lys Val Ala
                20                  25

(2) INFORMATION FOR SEQ ID NO:26:

(i) SEQUENCE CHARACTERISTICS:
             (A) LENGTH: 33 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:26:

Phe Val Lys Lys Val Ala Lys Val Ala Lys Lys Val Ala Lys Val
1               5                   10                  15

Ala Lys Lys Val Ala Lys Lys Val Ala Lys Lys Val Ala Lys Val
```

```
                     20                  25                  30
Ala Lys Lys (2) INFORMATION FOR SEQ ID NO:27:

(i) SEQUENCE CHARACTERISTICS:
         (A) LENGTH: 27 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:27:

Phe Val Lys Lys Val Ala Lys Val Ala Lys Lys Val Ala Lys Val
1               5                  10                  15

Ala Lys Lys Val Ala Lys Lys Val Lys Lys Lys
                20                  25

(2) INFORMATION FOR SEQ ID NO:28:

(i) SEQUENCE CHARACTERISTICS:
         (A) LENGTH: 32 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:28:

Phe Val Lys Lys Val Ala Lys Val Ala Lys Lys Val Ala Lys Val
1               5                  10                  15

Ala Lys Lys Val Ala Lys Lys Val Ala Lys Lys Val Ala Lys Lys
                20                  25                  30

Lys Lys (2) INFORMATION FOR SEQ ID NO:29:

(i) SEQUENCE CHARACTERISTICS:
         (A) LENGTH: 37 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:29:

Phe Val Lys Lys Val Ala Lys Val Ala Lys Lys Val Ala Lys Val
1               5                  10                  15

Ala Lys Lys Val Ala Lys Lys Val Ala Lys Lys Val Ala Lys Val
                20                  25                  30

Ala Lys Lys Lys Lys Lys Lys
                35

(2) INFORMATION FOR SEQ ID NO:30:
```

```
    (i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:30:

Phe Lys Val Lys Ala Lys Val Lys Ala Lys Val Lys Lys Lys Lys
1               5                  10                  15

Lys (2) INFORMATION FOR SEQ ID NO:31:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:31:

Phe Lys Val Lys Ala Lys Val Lys Ala Lys Val Lys Ala Lys Val
1               5                  10                  15

Lys Ala Lys Lys Lys Lys
                20

(2) INFORMATION FOR SEQ ID NO:32:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:32:

Phe Lys Val Lys Ala Lys Val Lys Ala Lys Val Lys Ala Lys Val
1               5                  10                  15

Lys Ala Lys Val Lys Ala Lys Val Lys Lys Lys Lys
                20                  25

(2) INFORMATION FOR SEQ ID NO:33:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear
```

(xi) SEQUENCE DESCRIPTION: SEQ ID NO:33:

Phe Lys Val Lys Ala Lys Val Lys Ala Lys Val Lys
1               5                  10

(2) INFORMATION FOR SEQ ID NO:34:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:34:

Phe Lys Val Lys Ala Lys Val Lys Ala Lys Val Lys Ala Lys Val
1               5                  10                  15

Lys Ala (2) INFORMATION FOR SEQ ID NO:35:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:35:

Phe Lys Val Lys Ala Lys Val Lys Ala Lys Val Lys Ala Lys Val
1               5                  10                  15

Lys Ala Lys Val Lys Ala Lys Val
                20

(2) INFORMATION FOR SEQ ID NO:36:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:36:

Lys Lys Lys Lys Phe Lys Val Lys Ala Lys Val Lys Ala Lys Val
1               5                  10                  15

Lys (2) INFORMATION FOR SEQ ID NO:37:

(i) SEQUENCE CHARACTERISTICS:
        (A) LENGTH: 21 amino acids
        (B) TYPE: amino acid
        (C) STRANDEDNESS:

(D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:37:

Lys Lys Lys Lys Phe Lys Val Lys Ala Lys Val Lys Ala Lys Val
1               5                  10                  15

Lys Ala Lys Val Lys Ala
            20

(2) INFORMATION FOR SEQ ID NO:38:

(i) SEQUENCE CHARACTERISTICS:
             (A) LENGTH: 27 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:38:

Lys Lys Lys Lys Phe Lys Val Lys Ala Lys Val Lys Ala Lys Val
1               5                  10                  15

Lys Ala Lys Val Lys Ala Lys Val Lys Ala Lys Val
            20                  25

(2) INFORMATION FOR SEQ ID NO:39:

(i) SEQUENCE CHARACTERISTICS:
             (A) LENGTH: 23 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:39:

Phe Ala Leu Ala Leu Lys Ala Leu Lys Lys Ala Leu Lys Lys Leu
1               5                  10                  15

Lys Lys Ala Leu Lys Lys Ala Leu
            20

(2) INFORMATION FOR SEQ ID NO:40:

(i) SEQUENCE CHARACTERISTICS:
             (A) LENGTH: 23 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:40:

Leu Ala Lys Lys Leu Ala Lys Lys Leu Lys Lys Leu Ala Lys Lys

```
                 1               5              10              15
Leu Ala Lys Leu Ala Leu Ala Phe
                                20

(2) INFORMATION FOR SEQ ID NO:41:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:41:

Phe Ala Phe Ala Phe Lys Ala Phe Lys Lys Ala Phe Lys Lys Phe
1               5              10              15
Lys Lys Ala Phe Lys Lys Ala Phe
                                20

(2) INFORMATION FOR SEQ ID NO:42:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:42:

Phe Ala Ile Ala Ile Lys Ala Ile Lys Lys Ala Ile Lys Lys Ile
1               5              10              15
Lys Lys Ala Ile Lys Lys Ala Ile
                                20

(2) INFORMATION FOR SEQ ID NO:43:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: linear (xi) SEQUENCE DESCRIPTION: SEQ ID NO:43:

Phe Ala Lys Lys Phe Ala Lys Lys Phe Lys Lys Phe Ala Lys Lys
1                       10              15              20
Phe Ala Lys Phe Ala Phe Ala Phe
                                20

(2) INFORMATION FOR SEQ ID NO:44:

(i) SEQUENCE CHARACTERISTICS:
        (A) LENGTH: 17 amino acids
        (B) TYPE: amino acid
```

-continued

```
            (C) STRANDEDNESS:
            (D) TOPOLOGY: linear (ii) MOLECULE TYPE: peptide (iii) HYPOTHETICAL: NO (xi) SEQUENCE DESCRIPTION: SEQ ID NO:44:

Phe Lys Arg Leu Ala Lys Ile Lys Val Leu Arg Leu Ala Lys Ile
1               5                   10                  15

Lys Arg (2) INFORMATION FOR SEQ ID NO:45:

(i) SEQUENCE CHARACTERISTICS:
            (A) LENGTH: 37 amino acids
            (B) TYPE: amino acid
            (C) STRANDEDNESS:
            (D) TOPOLOGY: linear (ii) MOLECULE TYPE: peptide (iii) HYPOTHETICAL: NO (xi) SEQUENCE DESCRIPTION: SEQ ID NO:45:

Lys Leu Lys Leu Ala Val Lys Leu Val Gly Leu Leu Arg Lys Lys
1               5                   10                  15

Arg Ala Leu Lys Ile Ala Leu Arg Gly Val Ala Lys Arg Ala Gly
                20                  25                  30

Arg Leu Ala Val Arg Lys Phe
                35

(2) INFORMATION FOR SEQ ID NO:46:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (iii) HYPOTHETICAL: NO (xi) SEQUENCE DESCRIPTION: SEQ ID NO:46:

Phe Ala Arg Ala Arg Lys Ala Arg Lys Lys Ala Arg Lys Lys Arg
1               5                   10                  15

Lys Lys Ala Arg Lys Lys Ala Arg Lys Asp Arg
                20                  25
```

METHOD OF ENHANCING WOUND HEALING BY STIMULATING FIBROBLAST AND KERATINOCYTE GROWTH IN VIVO, UTILIZING AMPHIPATHIC PEPTIDES

CROSS-REFERENCE TO RELATED APPLICATIONS

This is a continuation of application Ser. No. 08/231,730, filed Apr. 20, 1994, now U.S. Pat. No. 5,561,107 which in turn is a continuation-in-part of application Ser. No. 08/225,476, filed Apr. 8, 1994 in the names of Jesse M. Jaynes and Gordon R. Julian, now abandoned which in turn is a continuation-in-part of application Ser. No. 08/039,620, filed Jun. 4, 1993 in the names of Jesse M. Jaynes and Gordon R. Julian, now abandoned and also a continuation-in-part of application Ser. No. 08/148,889, filed Nov. 8, 1993 in the name of Gordon R. Julian, now abandoned as well as a continuation-in-part of application Ser. No. 08/148,491, filed Nov. 8, 1993 in the name of Gordon R. Julian, now abandoned.

BACKGROUND OF THE INVENTION

1. Field of the Invention

The present invention relates to a method of enhancing wound healing by stimulating fibroblast and keratinocyte growth in vivo, to a method of stimulating the accelerated growth of dermal tissue in a tissue culture containing same, utilizing amphipathic peptides, and to novel synthetic amphipathic peptides for carrying out such methodology.

2. Description of the Related Art

The use of topical antibacterial agents in conjunction with early wound excision and grafting has dramatically reduced the incidence of burn wound sepsis following massive thermal injury.

However, a major disadvantage associated with the use of the most effective topical antimicrobial agents such as Sulfamylon® and Silvadene® in burn or other wound treatment, is that such antimicrobial agents are cytotoxic to fibroblasts and keratinocytes. In consequence, these antimicrobial agents, while efficacious to reduce wound sepsis, in fact oppose dermal/tissue growth and regeneration to an unsatisfactory extent.

Accordingly, it would be a significant advance in the art, and is accordingly an object of the present invention, to provide a therapeutic agent for the treatment of wounds which promotes dermal/tissue growth and regeneration, and which may be used in conjunction with the aforementioned topical antimicrobial formulations.

Other objects and advantages of the present invention will be more fully apparent from the ensuing disclosure and appended claims.

SUMMARY OF THE INVENTION

The present invention relates to a method of treating wounds of mammalian subjects in need of such treatment, to promote wound healing thereof, comprising administering to the subject, e.g., by topically administering to the wound locus, a composition comprising a fibroblast and keratinocyte proliferatingly effective amount of an amphipathic peptide.

Preferably, the amount of the amphipathic peptide is also antimicrobially effective in amount, since the amphipathic peptides are surprisingly and unexpectedly microbicidal in character at concentrations which are in the general range of those which wound-healing promotion effects of such peptides are exhibited.

As used herein, the term "fibroblast and keratinocyte proliferatingly effective amount of an amphipathic peptide" means an amount of an amphipathic peptide which in application to the wound locus functions to promote the growth (as measured by increase in cell count) of fibroblasts and keratinocytes.

The growth of fibroblasts and keratinocytes may readily be determined by cell counts of these cells using a conventional cell counter means, e.g., a flow cytometer or a Coulter counter (Coulter Electronics, Inc., Hialeah, Florida) in a culture of such cells treated with one or more amphipathic peptides, as measured against a corresponding culture sample of the same type cells, which is not treated with the amphipathic peptide(s).

As used herein, the term "antimicrobially effective" means that the amphipathic peptide is microbicidal at the wound locus to bacteria selected from the group consisting of *Staphylococcus aureus, Pseudomonas aeruginosa,* Enterococcus species, and *Xanthomonas maltophilia,* and mixtures thereof. The microbicidal character of the amphipathic peptide(s) to these bacterial species can be readily determined by the analytical method set out hereinafter in Example 1 hereof.

As used herein, the term "amphipathic" in application to a peptide or class of peptides means peptide(s) which contain hydrophilic and hydrophobic amino acid moieties (side chains) which are oriented in relation to one another so that the peptide(s) have discrete hydrophilic and hydrophobic faces or regions defined by a multiplicity of the respective hydrophilic and hydrophobic side chains. For example, when the peptide is in an amphipathic alpha-helix conformation, the hydrophobic amino acid side chains are oriented on one face of the alpha helix while the hydrophilic amino acid side chains are oriented on the other face of the alpha helix. When the peptide is amphipathic and exists (in solution) in a beta-pleated sheet conformation, the peptide likewise exhibits hydrophobic and hydrophilic faces deriving from the alignment of the oriented amino acid side chains of the molecule.

As used herein, the term "defensin-class peptide" means either a natural defensin peptide which is provided in isolated form as an active ingredient of the composition employed for wound healing treatment in accordance with the present invention, or else a synthetic peptide which is homologous to the natural defensin peptide, containing between 17 and 39 amino acids along its length, and forming amphipathic beta-pleated sheets in solution.

A wide variety of amphipathic peptides may be effectively utilized in the broad practice of the present invention, including, but not limited to, natural and synthetic melittin-class, cecropin-class, magainin-class, and defensin-class peptides.

The beta pleated sheet conformation of peptides potentially usefully employed in the broad practice of the present invention may be readily determined by the circular dichroism technique described in Proteins, Creighton, Thomas E., W. H. Freeman & Co., New York (1984), pp. 179–182.

In another aspect, the present invention relates to a method of stimulating the accelerated growth of dermal tissue in a tissue culture containing same, comprising applying to the tissue culture a fibroblast and keratinocyte proliferatingly effective amount of an amphipathic peptide. Such methodology may for example be employed to produce skin for skin grafting purposes, utilizing a dermal tissue culture containing dermal tissue material of a skin graft recipient.

Other aspects and features of the present invention will be more fully apparent from the ensuing disclosure and appended claims.

DETAILED DESCRIPTION OF THE INVENTION, AND PREFERRED EMBODIMENTS THEREOF

The disclosures of prior copending U.S. patent application Ser. No. 08/225,476 filed Apr. 8, 1994 in the names of Jesse M. Jaynes and Gordon R. Julian for "METHOD OF COMBATING MAMMALIAN NEOPLASIA, AND LYTIC PEPTIDES THEREFOR," now abandoned U.S. patent application Ser. No. 08/039,620 filed Jun. 4, 1993 in the names of Jesse M. Jaynes and Gordon R. Julian, now abandoned U.S. patent application Ser. No. 08/148,889 filed Nov. 8, 1993 in the name of Gordon R. Julian, now abandoned and U.S. patent application Ser. No. 08/148,491 filed Nov. 8, 1993 in the name of Gordon R. Julian, now abandoned are all hereby incorporated herein by reference in their entirety.

The present invention is based on the surprising and unexpected discovery that amphipathic peptides may be advantageously employed to stimulate the proliferative growth of fibroblasts and epithelial cells such as keratinocytes, to thereby effect enhanced wound healing in mammalian subjects, and the further surprising and fortuitous finding that the amphipathic peptides have such dermal cell growth-promoting properties at concentrations which concomitantly have antimicrobial efficacy, against microbial species including those which cause or otherwise mediate sepsis and wound infection.

Defensins are a particularly preferred class of natural and synthetic peptides that are usefully employed in the practice of the invention and that have been discovered to possess a broad bactericidal spectrum as well as being mitogenic for fibroblasts and epithelial cells. These defensin-class peptides are arranged over at least a portion of their length (of amino acid sequence) so that the sucessive amino acid side chains are alternatingly hydrophobic (on one face of the molecule) and hydrophilic (on the other face of the molecule).

Naturally occurring amphipathic peptides play an important if not critical role as immunological agents in insects and have some, albeit secondary, defense functions in a range of other animals. The function of these peptides is to destroy prokaryotic and other non-host cells by disrupting the cell membrane and promoting cell lysis. Common features of these naturally occurring amphipathic, lytic peptides include an overall basic charge, a small size (23–39 amino acid residues), and the ability to form amphipathic α-helices. Among the various types of amphipathic lytic peptides that have been identified and are usefully employed in the broad practice of the invention are: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an (α-amphipathic helix and positive charge density are features that appear to participate in the function of the lytic peptides.

Active analogs of naturally occurring lytic peptides have been produced and tested in vitro against a variety of prokaryotic and eukaryotic cell types (see for example Arrowood, M. J., et al. J. Protozool. 38: 161s [1991]; Jaynes, J. M., et al. FASEB J. 2: 2878 [1988]), including: gram positive and gram negative bacteria, fungi, yeast, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells.

The specificity of the lytic action depends upon the sequence and structure of the peptide, the concentration of the peptide, and the type of membrane with which it interacts. Jaynes et al. Peptide Research. 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; However, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in the sensitivity to lysis of microbial pathogens (high sensitivity), transformed mammalian cells (high sensitivity), and normal mammalian cells (resistant), amphipathic peptide concentration can be manipulated to effect lysis of one cell type but not another at the same locus.

Synthetic peptide analogs can also act as agents of eukaryotic cell proliferation. Amphipathic peptides that promote lysis of transformed cells will, at lower concentrations, promote cell proliferation in some cell types. This stimulatory activity is thought to depend on the channel-forming capability of the amphipathic peptides, which somehow stimulates nutrient uptake, calcium influx or metabolite release, thereby stimulating cell proliferation (see Jaynes, J. M. Drug News & Perspectives 3: 69 [1990]; and Reed, W. A. et al. Molecular Reproduction and Development 31: 106 [19921]). Thus, at a given concentration, these peptides stimulate or create channels that can be beneficial to the normal mammalian cell in a benign environment where it is not important to exclude toxic compounds.

The synthetic amphipathic peptide analogs typically contain as few as 15 and as many as 40 amino acid residues. A phenylalanine residue is often present at the amino terminus of the protein to provide an aromatic moiety analogous to the tryptophan residue located near the amino terminus of natural cecropins, and a UV-absorbing moiety with which to monitor the purification of the synthetic peptide. The basis for the design of these lytic peptide analogs is that an amphipathic peptide of minimal length and containing overall positive charge density effects lytic activity.

The foregoing facts do not, however, suggest that amphipathic peptides could be satisfactorily used for wound healing applications, or for enhancing the growth of fibroblast and keratinocyte cells, and they do not suggest that antimicrobially effective amounts of amphipathic peptides are efficacious in the promotion of wound healing.

The present invention also contemplates a method of stimulating the accelerated growth of dermal tissue in a tissue culture containing same, comprising applying to the tissue culture a fibroblast and keratinocyte proliferatingly effective amount of an amphipathic peptide. Such methodology may for example be employed to produce skin for skin grafting purposes, utilizing a dermal tissue culture containing dermal tissue material of a skin graft recipient.

Such methodology thereby obviates the problems inherent in the slow growth of skin, and problems of sourcing of suitable skin graft material free of immunological rejection where the skin graft recipient has inadequate skin for grafting (e.g., in the instance where the extensiveness of burn damage has eliminated the recipient's own skin as a possible graft source).

The invention contemplates the in vivo treatment of dermatological and histological conditions as well as the in vitro usage of amphipathic peptides for assay or analytical purposes. In corporeal (in vivo) usage, the amphipathic peptides of the present invention may be delivered to the corporeal treatment site by any suitable method of delivery efficacious therefor.

In the treatment of gastrointestinal conditions, e.g., ulceration of the stomach or intestinal tract, the peptides delivered to the gastrointestinal locus may be "latently lytic", i.e., non-lytic prior to action at the internal site, but activated in vivo, under local conditions at the corporeal site, so as not to affect normal gastrointestinal flora or metabolic order. Alternatively, the amphipathic peptides may be inherently stabilized so as to be proteolytically resistant (due to chemical modification) to accommodate oral delivery thereof. Peptides delivered to an internal locus in active lytic form may usefully exhibit broad spectrum lytic activity for lysing pathogenic bacteria and virally infected cells, as well as transformed neoplastic cells, and thereby effect an enhanced therapeutic result, in addition to stimulation of fibroblasts and keratinocytes.

Amphipathic peptides of the present invention are useful in treating animals, e.g., mammals such as humans, for conditions in which stimulation of fibroblast and keratinocyte growth in vivo is desired, and for which the peptides are therapeutically effective.

A method of producing a fibroblast and keratinocyte growth-stimulating in vivo response in an animal subject in need of such treatment comprises administering to the animal subject a fibroblast and keratinocyte growth-stimulatingly effective amount of a composition including an effective amphipathic peptide.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered therapeutic composition containing amphipathic peptides of the invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific application, condition, or state involved, as readily determinable within the skill of the art, suitable therapeutic doses of the active lytic peptide agent, as delivered to the targeted corporeal site, and for achievement of therapeutic benefit will generally be in the range of 0.05 to 15 milligrams (mg) per kilogram body weight of the recipient per day, preferably in the range of 0.10 $\mu$g to 5.0 mg per kilogram body weight per day, and most preferably in the range of 0.5 $\mu$g to 2.5 mg per kilogram body weight per day. The desired dose is preferably presented as two, three, four, five, six, or more sub-doses administered at appropriate intervals throughout the day. These sub-doses may be administered in unit dosage forms, for example, containing from 0.01 to 1.5 mg, and preferably from 0.025 to 1.25 mg of active ingredient per unit dosage form. Alternatively, if the condition of the recipient so requires, the doses may be administered as a continuous infusion, via iv perfusion, osmotic pump or transdermal delivery techniques, or by direct injection into or topical administration to the corporeal site requiring treatment.

The mode of administration and dosage forms will of course affect the therapeutic amounts of the compounds which are desirable and efficacious for the given treatment application.

For example, orally administered dosages (where the lytic peptide is stabilized, either inherently as synthesized or via post-formation modification, against proteolytic (e.g., gastric) disgestion, e.g., by the modifications disclosed in prior copending U.S. patent application Ser. No. 08/148,491 filed Nov. 8, 1993, now abandoned the disclosures of which are hereby incorporated herein by reference, and such stabilized peptide is lytically active at the neoplastic site) typically are at least twice, e.g., 2–10 times, the dosage levels used in parenteral administration methods, for the same lytic peptide active ingredient. Intrathecal administration dosage levels generally are on the order of about 10% of the levels characteristic of parenteral administration dosage levels.

In general, adminstration levels of the lytic peptide therapeutic agents of the invention of more than about 15 milligrams per kilogram body weight per day are to be avoided, to maintain a conservative dosage level below the $ALD_{iv}$ of 40 milligrams per kilogram of body weight per day. It is noted that there is no determinate intramuscular approximate lethal dose ($ALD_{im}$). In preferred practice, the lytic peptide in a suitable formulation is administered by topical administration means and methods, and/or by cutaneous injection into the dermal tissue. Alternatively, other direct modes of administration may be employed. For example, iv perfusion may be used to introduce the lytic peptide to the corporeal site. As a further alternative, as osmotic pump may be placed in the vicinity of, or within, the corporeal tissue to be treated, and arranged to selectively release the lytic peptide, on a continuous, or non-continuous basis, to the tissue treatment site.

In the case of cutaneous tissue treatment, topical or transdermal delivery means and method are most preferably employed, and transdermal means such as transdermal patches may be utilized to deliver the amphipathic peptide to the corporeal treatment site.

The present invention also contemplates pharmaceutical formulations, both for veterinary and for human medical use, which comprise as the active agent one or more amphipathic peptidet(s) of the invention, as well as the use of an amphipathic peptide of the invention in the manufacture of a medicament for the treatment or prophylaxis of the dermal or other conditions variously described herein.

In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, nasal, ophthalmic, subcutaneous, intramuscular, intravenous, transdermal, intrathecal, intra-articular, intra-arterial, subarachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

The specific mode of delivery and administration of the amphipathic peptides of the present invention will depend on the specific corporeal site to be treated. In a given application, the optimum delivery route may differ depending on the form and stage of the cancer being treated. One potentially useful route is intravenous administration, which is the route by which most chemotherapeutic drugs are administered at present. Intra-arterial administration permits the introduction of the therapeutic agent(s) into the blood supply flowing directly to a tumor site, so that the agent(s) are delivered to the site prior to complete dilution in the total blood volume and prior to passage through the liver.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The features and advantages of the invention are more fully shown by the following illustrative examples and embodiments, which are not to be limitingly construed as regards the broad scope, utility, and applicability of the invention.

EXAMPLE 1

Representative Amphipathic Peptides

Set out in Table 1 below as illustrative examples of amphipathic peptide analogs of the present invention are the amino acid sequences of a family of related peptide analogs. The peptides may be synthesized according to conventional methods using a Milligen™ solid phase peptide synthesizer. Representative peptides from this group in some instances, are glyoxylated or methylated to stabilize same against proteolytic digestion, and used in subsequent experimental examples. The three letter amino acid symbols are as follows: Ala, alanine; Arg, arginine; Asp, aspartate; Gly, glycine; lle, lleleucine; Leu, leucine; Lys, lysine; Phe, phenylalanine; and Val, valine. These amphipathic peptide analogs are designated for ease of reference as SEQ ID NO. 1–46.

TABLE 1

PEPTIDE SEQUENCES

| | | |
|---|---|---|
| Phe Ala Val Ala Val Lys Ala Val Lys Lys Ala Val Lys Lys Val Lys<br>1              5                    10                 15<br>Lys Ala Val Lys Lys Ala Val Lys Lys Lys<br>            20               25 | SEQ ID NO: 1 |
| Phe Ala Val Ala Val Lys Ala Val Ala Val Lys Ala Val Lys Lys Ala<br>1              5                    10                 15<br>Val Lys Lys Val Lys Lys Ala Val Lys Lys Ala Val Lys Lys Lys<br>            20               25               30 | SEQ ID NO: 2 |
| Phe Ala Val Ala Val Lys Ala Val Ala Val Lys Ala Val Ala Val Lys<br>1              5                    10                 15<br>Ala Val Lys Lys Ala Val Lys Lys Val Lys Lys Ala Val Lys Lys Ala<br>            20               25               30<br>Val Lys Lys Lys<br>            35 | SEQ ID NO: 3 |
| Phe Ala Val Ala Val Lys Ala Val Lys Lys Ala Val Lys Lys Val Lys<br>1              5                    10                 15<br>Lys Ala Val Lys Lys Ala Val<br>            20 | SEQ ID NO: 4 |
| Phe Ala Val Ala Val Lys Ala Val Ala Val Lys Ala Val Lys Lys Ala<br>1              5                    10                 15<br>Val Lys Lys Val Lys Lys Ala Val Lys Lys Ala Val<br>            20               25 | SEQ ID NO: 5 |
| Phe Ala Val Ala Val Lys Ala Val Ala Val Lys Ala Val Ala Val Lys<br>1              5                    10                 15<br>Ala Val Lys Lys Ala Val Lys Lys Val Lys Lys Ala Val Lys Lys Ala<br>            20               25               30<br>Val | SEQ ID NO: 6 |
| Phe Ala Val Gly Leu Arg Ala Ile Lys Arg Ala Leu Lys Lys Leu Arg<br>1              5                    10                 15<br>Arg Gly Val Arg Lys Val Ala Lys Arg Lys Arg<br>            20               25 | SEQ ID NO: 7 |
| Phe Ala Val Gly Leu Arg Ala Ile Lys Arg Ala Leu Lys Lys Leu Arg<br>1              5                    10                 15<br>Arg Gly Val Arg Lys Val Ala<br>            20 | SEQ ID NO: 8 |
| Lys Arg Lys Arg Ala Val Lys Arg Val Gly Arg Arg Leu Lys Lys Leu<br>1              5                    10                 15<br>Ala Arg Lys Ile Ala Arg Leu Gly Val Ala Phe<br>            20               25 | SEQ ID NO: 9 |
| Ala Val Lys Arg Val Gly Arg Arg Leu Lys Lys Leu Ala Arg Lys Ile<br>1              5                    10                 15<br>Ala Arg Leu Gly Val Ala Phe<br>            20 | SEQ ID NO: 10 |
| Phe Ala Val Gly Leu Arg Ala Ile Lys Arg Ala Leu Lys Lys Leu<br>1              5                    10                 15 | SEQ ID NO: 11 |

TABLE 1-continued

PEPTIDE SEQUENCES

```
Arg Arg Gly Val Arg Lys Val Ala Lys Arg Lys Arg Lys Asp Leu
            20              25              30

Phe Ala Val Gly Leu Arg Ala Ile Lys Arg Ala Leu Lys Lys Leu       SEQ ID NO: 12
1               5               10              15

Arg Arg Gly Val Arg Lys Val Ala Lys Asp Leu
            20              25

Lys Arg Lys Arg Ala Val Lys Arg Val Gly Arg Arg Leu Lys Lys       SEQ ID NO: 13
1               5               10              15

Leu Ala Arg Lys Ile Ala Arg Leu Gly Val Ala Phe Lys Asp Leu
            20              25              30

Ala Val Lys Arg Val Gly Arg Arg Leu Lys Lys Leu Ala Arg Lys Ile   SEQ ID NO: 14
1               5               10              15

Ala Arg Leu Gly Val Ala Phe Lys Asp Leu
            20              25

Lys Lys Lys Lys Phe Val Lys Val Ala Lys Val Lys Lys               SEQ ID NO: 15
1               5               10              15

Val Ala Lys Lys Val Ala Lys Val Ala Val
            20              25

Lys Lys Lys Lys Phe Val Lys Val Ala Lys Val Lys Lys               SEQ ID NO: 16
1               5               10              15

Val Ala Lys Lys Val Ala Lys Val Ala Val Ala Lys Val Ala Val
            20              25              30

Lys Lys Lys Lys Phe Val Lys Val Ala Lys Val Lys Lys               SEQ ID NO: 17
1               5               10              15

Val Ala Lys Lys Val Ala Lys Val Ala Val Ala Lys Val Ala Lys
            20              25              30

Val Ala Val Ala Val
            35

Phe Val Lys Lys Val Ala Lys Lys Val Lys Lys Val Ala Lys Lys       SEQ ID NO: 18
1               5               10              15

Val Ala Lys Val Ala Val Ala Val
            20

Phe Val Lys Lys Val Ala Lys Lys Val Lys Lys Val Ala Lys Lys       SEQ ID NO: 19
1               5               10              15

Val Ala Lys Val Ala Val Ala Lys Val Ala Val Ala Val
            20              25

Phe Val Lys Lys Val Ala Lys Lys Val Lys Lys Val Ala Lys Lys       SEQ ID NO: 20
1               5               10              15

Val Ala Lys Val Ala Val Ala Lys Val Ala Lys Val Ala Val Ala Val
            20              25              30

Lys Lys Lys Lys Phe Val Lys Val Ala Lys Val Ala Lys Lys           SEQ ID NO: 21
1               5               10              15

Val Ala Lys Val Ala Lys Lys Val Ala Lys Lys Val
            20              25

Lys Lys Lys Lys Phe Val Lys Val Ala Lys Val Ala Lys Lys           SEQ ID NO: 22
1               5               10              15

Val Ala Lys Val Ala Lys Lys Val Ala Lys Lys Val Ala Lys Lys Val Ala
            20              25              30

Lys Lys Lys Lys Phe Val Lys Val Ala Lys Val Ala Lys Lys           SEQ ID NO: 23
1               5               10              15

Val Ala Lys Val Ala Lys Lys Val Ala Lys Lys Val Ala Lys Lys Val Ala
            20              25              30
```

TABLE 1-continued

PEPTIDE SEQUENCES

Lys Val Ala Lys Lys
           35

Phe Val Lys Lys Val Ala Lys Val Ala Lys Lys Val Ala Lys Val Ala        SEQ ID NO: 24
1           5               10              15
Lys Lys Val Ala Lys Lys Val
           20

Phe Val Lys Lys Val Ala Lys Val Ala Lys Lys Val Ala Lys Val Ala        SEQ ID NO: 25
1           5               10              15
Lys Lys Val Ala Lys Lys Val Ala Lys Lys Val Ala
           20              25

Phe Val Lys Lys Val Ala Lys Val Ala Lys Lys Val Ala Lys Val Ala        SEQ ID NO: 26
1           5               10              15
Lys Lys Val Ala Lys Lys Val Ala Lys Lys Val Ala Lys Val Ala Lys Lys
           20              25              30

Phe Val Lys Lys Val Ala Lys Val Ala Lys Lys Val Ala Lys Val Ala        SEQ ID NO: 27
1           5               10              15
Lys Lys Val Ala Lys Lys Val Lys Lys Lys
           20              25

Phe Val Lys Lys Val Ala Lys Val Ala Lys Lys Val Ala Lys Val Ala        SEQ ID NO: 28
1           5               10              15
Lys Lys Val Ala Lys Lys Val Ala Lys Lys Val Ala Lys Lys Lys
           20              25              30

Phe Val Lys Lys Val Ala Lys Val Ala Lys Lys Val Ala Lys Val Ala        SEQ ID NO: 29
1           5               10              15
Lys Lys Val Ala Lys Lys Val Ala Lys Lys Val Ala Lys Val Ala Lys
           20              25              30
Lys Lys Lys Lys Lys
           35

Phe Lys Val Lys Ala Lys Val Lys Ala Lys Val Lys Lys Lys Lys           SEQ ID NO: 30
1           5               10              15
Lys

Phe Lys Val Lys Ala Lys Val Lys Ala Lys Val Lys Ala Lys Val           SEQ ID NO: 31
1           5               10              15
Lys Ala Lys Lys Lys Lys
           20

Phe Lys Val Lys Ala Lys Val Lys Ala Lys Val Lys Ala Lys Val           SEQ ID NO: 32
1           5               10              15
Lys Ala Lys Val Lys Ala Lys Val Lys Lys Lys
           20              25

Phe Lys Val Lys Ala Lys Val Lys Ala Lys Val Lys                        SEQ ID NO: 33
1           5               10

Phe Lys Val Lys Ala Lys Val Lys Ala Lys Val Lys Ala Lys Val           SEQ ID NO: 34
1           5               10              15
Lys Ala

Phe Lys Val Lys Ala Lys Val Lys Ala Lys Val Lys Ala Lys Val           SEQ ID NO: 35
1           5               10              15
Lys Ala Lys Val Lys Ala Lys Val
           20

Lys Lys Lys Lys Phe Lys Val Lys Ala Lys Val Lys Ala Lys Val           SEQ ID NO: 36
1           5               10              15

TABLE 1-continued

PEPTIDE SEQUENCES

```
Lys

Lys Lys Lys Lys Phe Lys Val Lys Ala Lys Val Lys Ala Lys Val          SEQ ID NO: 37
1           5               10              15

Lys Ala Lys Val Lys Ala
                20

Lys Lys Lys Lys Phe Lys Val Lys Ala Lys Val Lys Ala Lys Val          SEQ ID NO: 38
1           5               10              15

Lys Ala Lys Val Lys Ala Lys Val Lys Ala Lys Val
                20              25

Phe Ala Leu Ala Leu Lys Ala Leu Lys Lys Ala Leu Lys Lys Leu          SEQ ID NO: 39
1           5               10              15

Lys Lys Ala Leu Lys Lys Ala Leu
                20

Leu Ala Lys Leu Ala Lys Lys Leu Lys Lys Leu Ala Lys Lys              SEQ ID NO: 40
1           5               10              15

Leu Ala Lys Leu Ala Leu Ala Phe
                20

Phe Ala Phe Ala Phe Lys Ala Phe Lys Lys Ala Phe Lys Lys              SEQ ID NO: 41
1           5               10

Phe Lys Lys Ala Phe Lys Lys Ala Phe
15              20

Phe Ala Ile Ala Ile Lys Ala Ile Lys Lys Ala Ile Lys Lys              SEQ ID NO: 42
1           5               10

Ile Lys Lys Ala Ile Lys Lys Ala Ile
15              20

Phe Ala Lys Lys Phe Ala Lys Lys Phe Lys Lys Phe Ala Lys Lys          SEQ ID NO: 43
1           5               10              15

Phe Ala Lys Phe Ala Phe Ala Phe
                20

Phe Lys Arg Leu Ala Lys Ile Lys Val Leu Arg Leu Ala Lys              SEQ ID NO: 44
1           5               10

Ile Lys Arg
15

Lys Leu Lys Leu Ala Val Lys Leu Val Gly Leu Leu Arg Lys Lys          SEQ ID NO: 45
1           5               10              15

Arg Ala Leu Lys Ile Ala Leu Arg Gly Val Ala Lys Arg Ala Gly Arg Leu Ala Val
                20              25              30

Arg Lys Phe
35

Phe Ala Arg Ala Arg Lys Ala Arg Lys Lys Ala Arg Lys Lys              SEQ ID NO: 46
1           5               10

Arg Lys Lys Ala Arg Lys Lys Ala Arg Lys Asp Arg
15              20              25
```

Chemical modification of amphipathic peptide analogs offers certain advantages. If the modifications are made in such a way that the peptides retain all or most of their amphipathic characteristics, then the physiologically active peptides have enhanced stability to proteolysis. With enhanced stability, oral delivery of the peptide is advantageously accommodated without excessive loss of activity due to proteolytic digestion. The stabilized lytic peptides of such type are suitably stabilized so as to remain resistant to proteolysis so that the peptide reaches the internal corporeal locus in an active condition. Alternatively, the amphipathic peptide may be originally synthesized in a stabilized form, or it may be chelated or otherwise coupled with an associated complexing agent so that the complexed peptide is initially non-lytically active in character, but under conditions existing at the desired corporeal locus the complexed composition dissociates or otherwise "unbinds" to provide the lytically active peptide for cell-proliferative activity at such locus.

Preferred amphipathic peptides within the general practice of the present invention include small (23–39 amino acid units) amphipathic cationic lytic peptides selected from those identified by amino acid sequences above. The effective peptides of the invention are naturally-occuring peptides or synthetic amphipathic peptides, and may be selected from natural and synthetic peptides of the classes of melittin, cecropin, magainin, and defensin peptides. Most preferred are defensin-class peptides.

The mechanism of action of the above-discussed peptides is not well understood. While we do not wish to be bound by any theory or hypothesis, it may be that the amphipathic nature of these peptides allows them to aggregate and interact with the plasma membrane to form pores that induce specific ion fluxes, including $Ca^{++}$. The specific effect of these peptides on different types of cells may possibly be due to the cytoskeletal differences between bacteria and mammalian cells, so that at a given concentration of peptide, fatal pores form in bacteria whereas growth stimulating pores form in mammalian cells.

Although the peptides of the present invention may be utilized at any safe and effective concentration, as is readily determinable within the skill of the art, peptide concentrations on the order of 1 nM to 10 μM may be suitable in various formulations for treatment in accordance with the teachings hereof.

The amphipathic peptides of the present invention may be usefully employed in dermal applications, for example stimulating the accelerated growth of the dermis in treatment of severe burns or more generally in woundtreatment, including post-operative wound healing applications.

EXAMPLE 2

Peptide Stabilization-Chemical Modification by Methylation

An exemplary and preferred reaction scheme for reductive alkylation of lysine residue ε-amino group and the N-terminal α-amino group is described below.

The preferred method for reductive alkylation uses pyridine borane as the reducing agent. This reagent is one of a class of reducing agents known as amine boranes. Pyridine borane exhibits a slightly higher reducing capacity than sodium cyanoborohydride, another reducing agent that can be used for the reductive alkylation. Pyridine borane drives the reductive alkylation reaction to complete dimethylation with no monomethyl products when excess reagents are used, as demonstrated by Wong, W. S. D., et aL Analytical Biochemistry 139: 58 (1984). While as much as 25% of cyanoborohydride goes to N-cyanomethyl products, lowering its methylation yield, pyridine borane does not appear to be involved in any such secondary reaction. In addition, sodium cyanoborohydride provides the potential hazard of contaminating the product with cyanide, severely limiting its use in therapeutic and in vivo applications. The alkylation reagent may suitably comprise formaldehyde as a methyl group (methylation) precursor. Shown below are the agents of reductive alkylation, formaldehyde and pyridine borane, the substrate, peptidyl lysine, and the chemical formulae of the reaction scheme species.

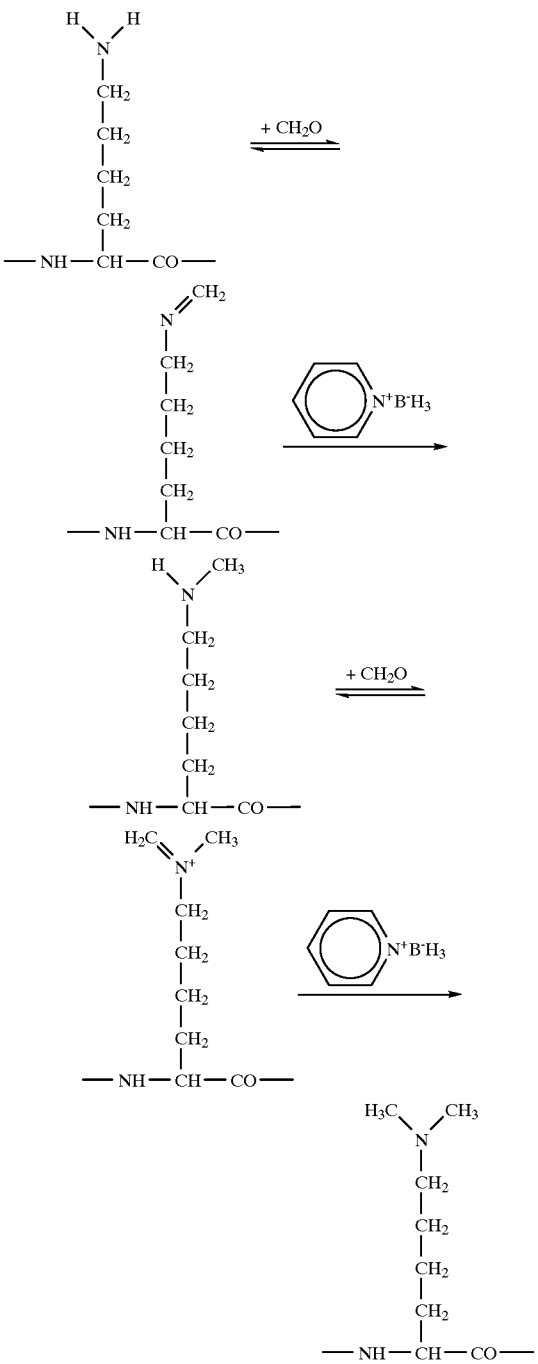

REACTION SCHEME 1:
DIMETHYLATION OF PEPTIDYL LYSINE

In the reductive alkylation reaction, 20 mg of a representative lysine containing a peptide taken from the group shown in Table 1 was dissolved in 1.6 ml 0.2 M HEPES buffer (N-2-hydroxyethylpeperazine-N'-2-ethane sulfonic acid), pH 7.0. While the mixture was stirring, 0.2 ml of 1.2 M pyridine borane (0.750 concentrated pyridine borane in 5 ml HPLC grade methanol) was added. Next, 0.2 ml of 0.726 M formaldehyde (0.6 ml 37% formaldehyde [HCHO] in 10 ml HEPES pH 7.0 buffer) was added to the mixture. A trace (approximately 1 μl) of 1-octanol was included in the reaction volume to control foaming. The reaction volume was then stirred for 2 hours at room temperature. After 2 hours the reaction mixture was titrated to below pH 3.0 with 0.2 M HCl. The reaction mixture was then frozen and lyophilized to reduce volume, and the resulting residue was washed 3 times with anhydrous ether to remove the pyridine borane. The reaction residue was reconstituted to approximately 2.0 ml with 0.1 M acetic acid and applied to a 2.4 cm×31 cm G-15-120μ Sephadex™ column to purify the reaction product. After the calibrated front eluted from the column (0.1 M acetic acid was the elution reagent), 20 ml of eluate containing the product was collected and the eluate was lyophilized to dryness.

The peptides were stored at −20° C. in the presence of a desiccant as their acetate salt. For use in the following examples they are dissolved in a saline buffer, pH 7.0, at a concentration of 0.1 mg/ml to 10 mg/ml.

EXAMPLE 3

Peptide Stabilization-Chemical Modification by Glyoxylation

An exemplary and preferred reaction scheme for glyoxylation of the guanido groups of arginine residues and the N-terminal (α-amino acid in a peptide taken from the group set out in Table 1 is described below.

Potential reagents which are capable of modifying the guanido group arginine with glyoxal under mild conditions and do not require an additional reduction reaction are 2,3-butanedione, phenylglyoxal, and glyoxal. The adducts from 2,3-butanedione and phenylglyoxal were judged to be too unstable, and glyoxal was therefore chosen as the preferred reagent for glyoxylation. The agent of glyoxylation, glyoxal, the substrate, peptidyl arginine, and the chemical reaction scheme are described below.

REACTION SCHEME 2:
GLYOXYLATION OF PEPTIDYL ARGININE

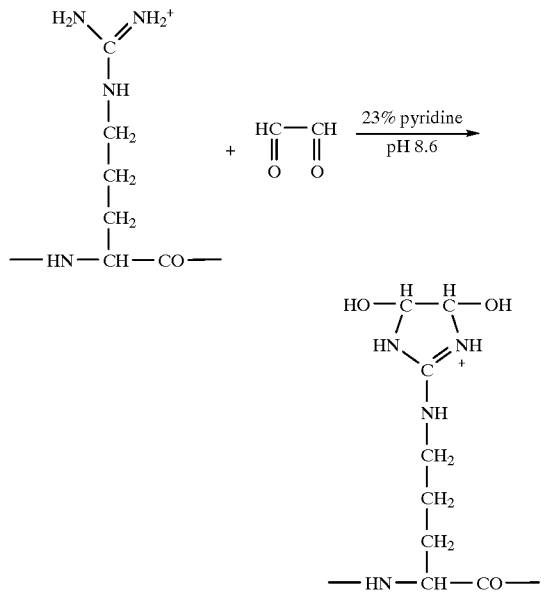

In the glyoxylation reaction, 5 mg of an arginine-containing peptide from the group shown in Table 1 was dissolved in 1.0 ml of 80% pyridine to form a clear solution. To this mixture 2 ml of 0.5 M sodium bicarbonate buffer pH 8.0 (NaHCO$_3$—NaOH) was added. Freshly prepared, 30% glyoxal suspension in the 0.5 M sodium bicarbonate buffer was added to the reaction volume and the cloudy reaction mixture was stirred at room temperature for three hours. After 20 minutes the solution became mostly clear although progressively yellow-brown during the course of the reaction. The final concentration of the pyridine was 23%. The pyridine, as a representative heterocyclic amine, was essential to the reaction, in order to maintain the glyoxal/peptide mixture in solution. Other water-soluble dielectric solvents such as the heterocyclic amine piperidine were tested and can be used in the place of pyridine.

At the conclusion of the reaction, glacial acetic acid was added drop-wise to bring the pH to 6.0. A two-phase extraction using three parts ether to one part acetone for the organic phase was repeated three times to remove the majority of the glyoxal. The pyridine was not removed to a significant extent. The preparation was dried in a lyophilizer and the crusty residue was rinsed with three parts ether to one part acetone. The residual ether-acetone was removed in vacuo. The cloudy ether-acetone supernatant was centrifuged to recover a precipitate which was pooled with the remaining residue by washing the tube with glacial acetic acid. The residue was dissolved in glacial acetic acid and a small amount of insoluble material was removed by centrifugation. The solution was then applied to a G-15-120 Sephadex™ column (2.4×31 cm) and eluted with 0.1 M acetic acid. The recovered fractions were lyophilized to dryness overnight.

The peptides were stored at −20° C. in the presence of a desiccant as their acetate salt. For use in the following examples they were dissolved in a saline buffer, pH 7.0 at a concentration of 0.1 mg/ml to 10 mg/ml.

EXAMPLE 4

In Vitro Lysis of Pathogenic Bacteria

The effect of a lytic peptide (Hecate-1, homologous to SEQ ID NO. 4) was tested against antibiotic-resistant pathogenic bacteria in vitro. In this test, antibiotic-resistant cultures of *Pseudomonas aeruginosa* and *Klebsiella pneumoniae* were obtained from deceased patients. The lytic peptide bioassay was performed as described below.

A flask containing 49 ml of nutrient broth was inoculated with 1 ml of an overnight culture of the test bacteria. The culture was allowed to grow to mid-log phase at 37° C. with shaking (approximately 4 hours). When the cells reached the correct density, the cells were transferred to a sterile tube and centrifuged for 10 minutes at 3000 rpm. The pellet was resuspended in 3 ml of phosphate buffer and centrifuged for 10 minutes at 3000 rpm. The pellet was resuspended once again in sufficient (but measured) volume to calculate the absorbance of the suspension at 600 nm. Using the resulting absorbance and a previously constructed growth curve, the required dilution to achieve a concentration of $10^6$ cells/ml was determined.

One micromole of the test peptide was dissolved in 1.0 ml of 0.01% acetic acid to make a 1 mM solution and serial dilutions were made to give a range of peptide concentrations from 10 μM to 1 mM. The test culture tubes for the bioassay contained 800 μl of phosphate buffer, pH 7.0, 100 μl of cells at $10^6$ cells/ml and 100 μl of peptide solution (10 μM to 1 mM). The final concentration of peptide in the assay was from 1 μM to 100 μM. A reaction system minus peptide was included as a control. The tubes were incubated at 37° C. for one hour.

After the incubation period, for each tube two 1:10 serial dilutions in phosphate buffer were made (three 1:10 serial dilutions for the control culture). 100 μl of each dilution was spread on an agar plate, in duplicate and incubated overnight at 37° C. The following day, the number of colonies on the control plates was counted to determine the starting number of cells in the assay tubes. The number of cells surviving the assay in the presence of peptide was also counted. The results are shown in Table 2.

TABLE 2

LYSIS OF PATHOGENIC BACTERIA WITH LYTIC PEPTIDE

| Species Minimal | No. of Independent Ilelates Tested | Average Inhibitory Concentration |
|---|---|---|
| Pseudomonas aeruginosa | 1 | 6.5 μM |
| Klebsiella pneumoniae | 4 | 9.9 μM |

The results show that a lytic peptide concentration in the range of 1 μm to 100 μM was effective for lysis of antibiotic resistant *Pseudomonas aeruginosa* and *Klebsiella pneumoniae*, most preferably in the range of 5 μM to 50 μM.

In a second experiment, antibiotic-resistant llelates of *Mycobacterium tuberculosis, Streptococcus pneumoniae, Pneumocystis carinii, Hemophilus influenzae, Klebsiella pneumoniae, Chlamydia pneumoniae,* and *Pseudomonas cepacia* are tested in the same bioassay for lytic activity. Peptide concentration in the range of 1 μm to 100 μM is effective for lysis of the tested pathogenic bacteria, most preferably in the range of 5 μM to 50 μM. This concentration of peptide will be compared with the amount required to treat the pulmonary epithelial cells in a non-toxic manner in order to develop an effective combination dose for concurrent treatment of CF and accompanying bronchopulmonary infections, as well as other pulmonary diseases.

EXAMPLE 5

In Vitro Toxicity of Peptide to Epithelial Cells

A lytic peptide and a chemically modified non-lytic peptide selected from the group shown in Table 1 are tested in vitro with normal and cystic fibrosis affected lung and gastrointestinal epithelial cells, and the cells are assayed for survival. Cell culture is performed according to standard protocols (see for example Reed, W. A. et al. Molecular Reproduction and Development 31: 106 [1992]), and the cytotoxicity assay by $^{51}$Cr release is performed as in Jaynes, J. M. et al. Peptide Research 2: 157 (1989). This test shows a range of peptide concentration that is non-toxic for the cells in vitro. The purpose of the experiment is to formulate a range of safe doses of peptide for in vitro and in vivo experiments. Peptide concentration above 100 μM to 500 μM is toxic for the epithelial cells.

EXAMPLE 6

In Vitro Effectiveness of Chloride Conductance in CF Epithelial Cells

A lytic peptide and a chemically modified non-lytic peptide selected from the group shown in Table 1 are tested in vitro for stimulation of chloride efflux with pulmonary and gastrointestinal epithelial cells, using a range of peptide concentration that is non-toxic to the cells as shown by the experiments in Example 5. The peptides used in this experiment are chemically modified and non-lytic, for the gastrointestinal epithelial cells, and non-modified, lytic peptides for the pulmonary epithelial cells.

The rationale for this experiment is based on previous experiments for cell proliferation (see Reed, W. A. et al. Molecular Reproduction and Development 31: 106 [1992]) which showed that for cultures of epithelial cells, application of peptide in the range of 10 μM to 50 μM stimulated cell growth. The hypothesis for the mechanism of cell growth is that the peptide caused the stimulation of alternative channels or the formation of new channels, providing for better passage of nutrients or metabolites. This hypothesis (e.g. channel formation or stimulation) is also suggested as the mechanism for stimulation of chloride efflux in normal and CF epithelial cells. The cells are cultured according to standard protocols as in Example 5, and chloride efflux is measured according to standard protocols.

Peptide concentration in the range of 1 μM to 50 μM is effective for stimulating chloride efflux from pulmonary and gastrointestinal epithelial cells. Combining the results of the pathogenic bacterial lysis experiment, the epithelial cell toxicity experiment, and the stimulation of chloride efflux experiment yields the following conclusion: a peptide concentration corresponding to 1 μM to 50 μM is the preferred range for treatment of CF affected epithelial cells, microbial infections and other disease states in vitro.

EXAMPLE 7

In Vivo Lysis of Pathogenic Bacteria in Infected Mice

The effect of a representative lytic peptide from the group shown in Table 1 is tested in mice that have bronchopulmonary infections of *Mycobacterium tuberculosis, Pseudomonas aeruginosa,* or *Pseudomonas cepacia.* Mice infected with both antibiotic-resistant and non-resistant bacteria are used, and treatment with antibiotics is compared to treatment with a lytic peptide. A concentration of peptide in the range of 10 μg to 25 mg per kg body weight for the recipient per day is the preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

An advantageous modality of in vivo pulmonary delivery of the peptide is via a liquid nebulizer inhaler device or a dry powder nebulizer inhaler device, depending on the physical state, solubility, and dosage of the peptide. Suitable nebulizers are commercially available under the trademarks "ROTAHALER", "SPINHALER", and "TURBOHALER". Another potentially suitable powder nebulizer apparatus and method of nebulization is disclosed in U.S. Pat. No. 5,186,166 to Riggs et al.

This experiment shows that peptide in the preferred range of 10 μg to 25 mg per kg body weight for the recipient per day is effective for treatment of mice with bronchopulmonary infections.

EXAMPLE 8

In Vivo Test of CF Mice Treated with Peptide at Pulmonary Site

The effect of a representative lytic, non-chemically modified peptide from Table 1 is tested on previously engineered transgenic mice that are homozygous for the CF defect. The peptide is delivered to a pulmonary locus as described in Example 7. A concentration of peptide in the range of 10 μg to 25 mg per kg body weight for the recipient per day is employed as the preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

The experiment shows that peptide in the preferred range of 10 μg to 25 mg per kg body weight for the recipient per day is effective for treatment of mice with bronchopulmonary infections.

EXAMPLE 9

In Vivo Test of CF Mice Treated with Modified Peptide at Gastrointestinal Site

The effect of a representative non-lytic, chemically modified peptide from Table 1 is tested on previously engineered transgenic mice that are homozygous for the CF defect, as described in Example 8. The peptide is orally delivered to the gastrointestinal locus, and the chemical modification (glyoxyiation or methylation) of the peptide confers enhanced proteolytic resistance, as described in Examples 2–3. A concentration of peptide in the range of 10 μg to 25 mg per kg body weight for the recipient per day is utilized as a preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

The experiment shows that peptide in the preferred range of 10 μg to 25 mg per kg body weight for the recipient per day is effective for treatment of mice with gastrointestinal problems due to CF.

Examples 4–9 described above, taken together, demonstrate that a non-toxic, effective dose of amphipathic peptide can be used to treat CF affected epithelia at pulmonary and gastrointestinal sites and resulting bronchopulmonary infections concurrently in vivo. In addition, various compounds of the present invention having appertaining therapeutic ability may be usefully employed in the treatment of other pulmonary disease states including: various neoplasias, bronchogenic cancers, pneumonia, bronchitis, bronchopulmonary viral infections, and bronchopulmonary microbial infections.

Further, the lytic peptides of the present invention may be usefully employed in the treatment of neoplasias as well as the concurrent treatment of other conditions for which the peptides are therapeutically useful, i.e., the administered peptide may effect neoplastic activity at the same time it is physiologically and/or pharmaceutically useful for the treatment of other conditions or disease states in the subject receiving treatment. Examples of such other conditions or disease states include microbial, parasitic and viral infections, dermal and subdermal wounds (as to which the peptide is healingly effective), etc.

The lytic peptides of the invention may suitably be utilized in combination with one another, as a mixture of selected different peptides, as well as in single peptide form. The use of multiple lytic peptide species may for example be beneficial when the neoplastic site contains multiple tumors of differing type, as to which different peptides of the invention are therapeutically effective.

EXAMPLE 10

Antineoplastic Activity—Mammalian Melanoma

In the following description, the peptide denoted DP-1 had the amino acid sequence identified hereinabove as SEQ. ID NO. 39 and the peptide denoted DP-2 had the amino acid sequence identified hereinabove as SEQ. ID NO. 40, and the control was saline.

Mouse melanoma cells were introduced onto the scapula of the test mice. Seventy two hours later, treatment was begun with ten mice in each treatment group. One group was administered DP-1 peptide, one group was administered DP-2 peptide, and the third group was administered saline control. Each treatment consisted of a 25 μg intraperitoneal injection of 0.1 ml volume once a day every other day for one week. Each mouse received four injections in total. The DP-2 group and the control group both showed death of all animals after 33 days, while the DP-1 group maintained a 62% survival rate through the 38 day study.

EXAMPLE 11

Toxicity Determination—Lytic Peptides

In the following description, the peptide denoted DP-1 had the amino acid sequence identified hereinabove as SEQ. ID NO. 39, the peptide denoted DP-1m had the same amino acid sequence identified hereinabove as SEQ. ID NO. 39 but was fully methylated to stabilize same against proteolysis in accordance with the methylation procedure as described hereinabove, the peptide denoted D5-C had the amino acid sequence identified hereinabove as SEQ. ID NO. 9, and the peptide denoted D5-F had the same amino acid sequence identified hereinabove as SEQ. ID NO. 2.

In the following description, Riv=iv administration in rat, Rim=intramuscular administration in rat, Miv=iv administration in mouse, and Mim=intramuscular administration in mouse.

Lethality data and clinical observations were collected during the ALD evulation of the peptides denoted D5-F, DP-1, DP-1m. The data presented below are complete for D5-F and DP-1. Since it was necesary to repeat the im assessment for DP-1m, due to poor solubility at the concentration required for im administration, the im findings for DP-1m are not presented below.

iv Assessment

For all three compounds, two replicates were performed with both mice and rats. In the first replicate, the animals (one animal/dose) were exposed to a range of doses, 10.0, 5.0, 2.5, 1.0, 0.5, 0.25, 0.1, 0.05, 0.025, and 0.01μM. For the second replicate, the lethal dose was diluted to produce an intermediate dose between the lethal dose and the subsequent nonlethal dose.

Mice Lethality and Clinical Observations

Lethality

Replicate 1: D5F and DP1 were lethal at 10.0 μM, whereas DP1m was not lethal at the same dose. No lethality resulted at the lower concentrations of D5F, DP1, and DP1m.

Replicate 2: For D5F and DP1, the high dose was diluted to 7.5 μM for the second replicate. The doses administered were 7.5, 5.0, 1.0, 0.5, 0.25, 0.1, 0.05, 0.025, and 0.01 μM. D5F was lethal at 7.5 μM, whereas DP1 was not. DP1m was again not lethal to the mice over the treatment levels delivered.

The effects of the highest dose (lethal-D5F and DP1, nonlethal-DP1m) were verified by dosing one animal with the effective or highest no effect concentration used in Replicate 1. In the case of D5F, the dose of 7.5 $\mu$M was used to verify lethality observed in Replicate 2. The mice treated with these compounds were previously exposed to the lowest dose 0.01 $\mu$M. The doses were the following: D5F, 7.5 $\mu$M; DP1, 10.0 $\mu$M; and DP1m, 10.0 $\mu$M. For all components, mice were dead within four hours after treatment.

The lethality for the two DP-1m formulations evaluated are not conclusive as to toxicity of DP-1m in mice.

Clincal Observations

One mouse exposed to 10 $\mu$M DP1m exhibited discoloration of the tail soon after dosing. In particular, the tails appeared to darken from the usual pink coloration to bluish purple. The appearance of the tail resembled a cyanotic condition. Later during the two-week postdosing period, the end of the tail of the animal exposed to 10 $\mu$M DP1m sloughed off and the remaining tail portion exhibited a blue-black coloration.

Rat Lethality and Clinical Observations

Lethality

Replicate 1: D5F, DP1, and DP1m were lethal at 10.0 $\mu$M. No lethality resulted at the lower concentrations.

Replicate 2: For all compounds, the high dose was diluted to 7.5 $\mu$M for the second replicate. The doses administered were 7.5, 5.0, 2.5, 1.0, 0.5. 0.25, and 0.1 $\mu$M. D5F, DP1, and DP1m were lethal at 7.5 $\mu$M and were not lethal at the lower doses.

The lethality of the high dose was verified by dosing one animal with the lethal dose determined by Replicate 1. The rats used for the evaluation were remaining from the original shipment and were naive for treatment. The doses were the following: D5F, 10.0 $\mu$M; DP1, 10.0 $\mu$M; and DP1m, 10.0 $\mu$M. For all compounds, the rats were deal within four hours after treatment.

Clinical Observations

Rats exposed to 2.5 and 5.0 $\mu$M D5F exhibited discoloration of the tail soon after dosing. In particular, the tails appeared to darken from the usual pink coloration to bluish purple. The appearance of the tail resembled a cyanotic condition. Later during the two-week postdosing period, the ends of the tails of the animals exposed to 2.5 and 5.0 $\mu$M of D5F sloughed off and the remaining tail portion exhibited a blue-black coloration.

Im Assessment

For D5F and DP1, two replicates were performed with rats. In the first replicate, the animals (one animal/dose) were exposed to a range of doses; 10.0, 1.0, 0.1, and 0.01 $\mu$M. The dose range used was smaller than that originally planned due to the availability of the compound to prepare an adequate amount of dosing solution.

Replicates 1 and 2: im administration of each compound produced no effects. No lethality or clinical observations were observed after dosing. Also, gross examination of the hind leg musculature at necropsy indicated no changes related to the im administration of the compounds.

Set out below in Table 3 below is a summary of the lethal concentration and clinical observations for peptides DP-1, DP-1m, D5-C, and D5-F.

| Peptide | [$\mu$M] T = 0 | $\mu$mol Riv | ug/dose | $\mu$mol Rim | ug/dose | $\mu$mol Miv | ug/dose |
|---|---|---|---|---|---|---|---|
| DP-1 | 7.5; 10.0 | 1.5 | 4,689.41 | not lethal | not lethal | 0.2 | 625.36 |
| DP-1m | 7.5; 10.0 | 1.5 | 5,139.41 | not lethal | not lethal | 0.2 | 685.36 |
| D5-C | 2.0; 2.5 | 0.4 | 1,269.78 | not lethal | not lethal | 0.05 | 158.72 |
| D5-F | 7.5 | 1.5 | 5,416.19 | not lethal | not lethal | 0.15 | 541.62 |

EXAMPLE 12

Antineoplastic Activity—Mammalian Melanoma

In the following description, the peptide denoted DP-1 had the amino acid sequence identified hereinabove as SEQ. ID NO. 39, the peptide denoted DP-1m had the same amino acid sequence identified hereinabove as SEQ. ID NO. 39 but was fully methylated to stabilize same against proteolysis in accordance with the methylation procedure as described hereinabove, the peptide denoted D5-C had the amino acid sequence identified hereinabove as SEQ. ID NO. 9, and the peptide denoted D5-F had the same amino acid sequence identified hereinabove as SEQ. ID NO. 12.

The above-identified peptides were tested in murine in vivo systems to determine the antineoplastic efficacy thereof, in accordance with a standard MTT assay to determine the resulting $ID_{50}$ values, with the results shown in Table 4 below.

TABLE 4

| Peptide Designation | Average MTT $ID_{50}$ Values in $\mu$M |
|---|---|
| DP-1 | 5.57 |
| DP-1m | 5.43 |
| D5-C | 5.32 |
| D5-F | 4.75 |

EXAMPLE 13

Antineoplastic Activity—Human Mammalian Neoplasias

Various peptides having sequences shown in Table 1 were tested for antineoplastic activity. The cells utilized in the testing with one exception (mouse melanoma cells) were human clinical isolates (obtained at University of North Carolina Memorial Hospital, Chapel Hill, N.C.) and were derived from the following tumors: MG-63—chemotherapy resistant osteosarcoma; T47D—hormone sensitive breast tumor; MDA-MB231—hormone insensitive breast tumor; BT474—hormone sensitive breast tumor; B16F1—mouse melanoma; and KBATCC—nasopharyngeal carcinoma.

The test procedure was a conventional MTT $ID_{50}$ assay. Tests were done in quadruplicate and data were tabulated for the average $\mu$M concentration necessary to achieve the $ID_{50}$ (ranging from about 2 to about 20 $\mu$g/ml).

The results of the testing of twenty different peptides numbered 1–20 is set out in Table 6 below, and Table 5 sets out the identity of such peptides with reference to the amino acid sequences thereof, with reference to sequences listed in Table 1 hereof.

TABLE 5

| SEQ. ID NO., Table I | Peptide Number Referenced in Table IV |
|---|---|
| 1 | 1 |
| 4 | 2 |
| 15 | 3 |
| 18 | 4 |
| 21 | 5 |
| 24 | 6 |
| 27 | 7 |
| 31 | 8 |
| 34 | 9 |
| 37 | 10 |
| 7 | 11 |
| 8 | 12 |
| 9 | 13 |
| 10 | 14 |
| 11 | 15 |
| 12 | 16 |
| 13 | 17 |
| 14 | 18 |
| 39[a] | 19 |
| 39[b] | 20 |

[a] this peptide was SEQ ID NO. 39 in an unmodified (non-stabilized against proteolysis) form thereof
[b] this peptide was SEQ ID NO. 39 in a modified fully methylated (stabilized against proteolysis) form thereof

TABLE 6

| Peptides | MG-63 | T47D | MDA231 | BT474 | B16F1 | KBATCC | Average |
|---|---|---|---|---|---|---|---|
| 1 | 10.00 | 2.20 | 10.00 | 10.00 | 5.60 | 5.10 | 7.15 |
| 2 | 10.00 | 6.00 | 10.00 | 10.00 | 5.80 | 8.40 | 8.37 |
| 3 | 10.00 | 4.30 | 10.00 | 7.40 | 6.00 | 6.50 | 7.37 |
| 4 | 10.00 | 4.90 | 10.00 | 7.50 | 5.80 | 5.60 | 7.30 |
| 5 | 10.00 | 6.20 | 10.00 | 10.00 | 10.00 | 9.60 | 9.30 |
| 6 | 10.00 | 6.30 | 10.00 | 10.00 | 10.00 | 10.00 | 9.38 |
| 7 | 10.00 | 6.20 | 10.00 | 10.00 | 10.00 | 6.30 | 8.75 |
| 8 | 10.00 | 8.40 | 10.00 | 10.00 | 10.00 | 10.00 | 9.73 |
| 9 | 10.00 | 9.30 | 10.00 | 10.00 | 10.00 | 10.00 | 9.88 |
| 10 | 10.00 | 2.90 | 10.00 | 10.00 | 10.00 | 10.00 | 8.82 |
| 11 | 10.00 | 10.00 | 10.00 | 10.00 | 10.00 | 8.90 | 9.82 |
| 12 | 10.00 | 10.00 | 10.00 | 10.00 | 10.00 | 5.60 | 9.27 |
| 13 | 5.90 | — | 10.00 | 6.80 | — | 5.60 | — |
| 14 | 6.40 | 4.60 | — | 10.00 | — | — | 5.73 |
| 15 | 6.10 | 4.30 | 10.00 | 8.80 | 7.70 | 7.30 | 7.37 |
| 16 | 5.90 | 2.00 | — | 6.20 | 5.10 | — | — |
| 17 | 6.90 | — | 9.20 | 6.30 | 8.50 | 5.40 | 6.22 |
| 18 | 10.00 | 4.40 | 10.00 | 7.70 | 10.00 | 6.10 | 8.03 |
| 19 | — | 4.80 | 5.90 | — | 5.90 | 5.40 | 5.57 |
| 20 | — | 3.40 | 6.40 | — | 6.40 | 5.70 | 5.43 |
| Average | 8.59 | 5.13 | 9.05 | 8.62 | 7.63 | 7.06 | |

*Please note that the two individual best peptides are in the cross-hatched boxes
**The two overall best peptides are cross-hatched and surrounded by lines in the "Average" column
***The numbers are MTT ID50 values in μM peptide concentration. The values listed as 10 are actually greater than 10.

The present invention also contemplates pharmaceutical formulations for human medical use, which comprise as one of the active agents therapeutic amounts of the peptides of Table 1 above as well as other physiologically active compounds. These formulations may for example include as additional components nebulizable compounds such as Survanta® TA pulmonary surfactant (Burroughs Wellcome Co.), Mucomist™ mucolytic agent (Mead-Johnson), Ribavirin™ virazole (TCN Pharmaceuticals), and DNase (Genentech), as well as other physiologically active therapeutic agents such as antibiotics.

EXAMPLE 14

Fibroblast and Keratinocyte Proliferating and Antimicrobial Activity

The antimicrobial activity and proliferative effect on fibroblast and keratinocyte cultures was determined using two synthetic defensin-class peptides.

Synthetic defensin-class peptides employed in the test included peptides denoted DM 1 (having the sequence SEQ. ID 31 set out hereinabove) and DM 2 (having the sequence SEQ. ID 34 set out hereinabove), are 17 and 21 amino acids long, respectively, and form amphipathic, beta pleated sheets in solution. The minimal inhibitory concentration (MIC) for each peptide for four to five different clinical isolates each of *Staphylococcus aureus* (A–E), *Pseudomonas aeruginosa* (F–J), *Enterococcus species* (K–O), and *Xanthomonas maltophilia* (P–S) was determined by macro-broth dilution.

A starting inoculum of $10^5$ cfu/ml for each strain was used and doubling dilutions of the peptides were tested in nutrient broth. MIC's for each peptide were determined after an overnight incubation at 35° C. The proliferative effect of each peptide was determined by measuring cell counts in triplicate cultures of either NIH 3T3 fibroblasts (3T3, inoculum $2\times10^4$ cells/well in 24 well plates). All media was supplemented with L-glutamine and 5% FCS. After initial plating, the media was changed and cultures were incubated an additional 96 hours in the presence of several different concentrations of peptide 25 μg/ml, 50 μg/ml, and 100 μg/ml). Cell counts were determined using a Coulter counter (Coulter Electronics, Inc., Hialeah, Fla.). Experimental cell counts were compared to control using Student's t-test.

The MIC for both peptides is shown in Table 7 below. The MIC for all strains of bacteria is low, 16 μg/ml or less in most instances.

TABLE 7

| PEPTIDE | Staphylococcus aureus | | | | | Pseudomonas aeruginosa | | | | |
|---|---|---|---|---|---|---|---|---|---|---|
|  | A | B | C | D | E | F | G | H | I | J |
| DM1 | 8 | 16 | 8 | 8 | 16 | 2 | 4 | 2 | 2 | 2 |
| DM2 | 4 | 4 | 16 | 8 | 8 | 2 | 4 | 4 | 2 | 4 |

| PEPTIDE | Enterococcus species | | | | | Xanthomonas Maltophilia | | | |
|---|---|---|---|---|---|---|---|---|---|
|  | K | L | M | N | O | P | Q | R | S |
| DM1 | 8 | 8 | 8 | 4 | 8 | >16 | >16 | 8 | >16 |
| DM2 | 8 | 8 | 4 | 16 | 16 | 8 | >16 | 8 | >16 |

Values expressed represent MIC (in μg/ml) for bacterial strains A–S.

The results of the cell count assays are shown in Table 8 below. No concentration of either DM1 or DM 2 resulted in decreased cell counts of 3T3 fibroblasts or human keratinocytes. On the contrary, most concentrations of DM 1 and DM 2 resulted in significantly greater cell counts in 3TC fibroblast cultures compared to control ($p<0.05$). Keratinocyte cell counts were elevated for both peptides, but only cultures incubated with DM 2 at a range of 50–100 μg/ml were significantly greater than control ($p<0.05$).

TABLE 8

|  | DM1 (μg/ml) | | | DM2 (μg/ml) | | | CONTROL |
|---|---|---|---|---|---|---|---|
|  | 25 | 50 | 100 | 25 | 50 | 100 | (NO PEP) |
| 3T3 | 6.6 ± 0.11 | 8.6* ± 0.24 | 10.6* ± 0.24 | 8.7* ± 0.50 | 8.0* ± 0.27 | 7.8* ± 0.13 | 6.8 ± 0.19 |
| HK | 2.7 ± 0.04 | 2.7 ± 0.08 | 2.9 ± 0.04 | 2.7 ± 0.06 | 3.1* ± 0.05 | 3.3* ± 0.09 | 2.6 ± 0.13 |

Values expressed as cell number ($\times 10^4$) ± SEM.
*$p < 0.05$ by Student t-test.

Finally, low concentrations (greater than 10 fold less that used clinically) of both Silvadene and Sulfamylon resulted in a significant decrease in 3T3 fibroblast cell counts as shown in Table 9 below.

TABLE 9

|  | Silvadene (%) 0.01 | Sulfamylon (%) 0.01 | CONTROL (NO PEP) |
|---|---|---|---|
| 3T3 | 3.9* ± 0.13 | 4.4* ± 0.15 | 6.8 ± 0.19 |

The results of these tests demonstrate that DM1 and DM2, two synthetic defensin-class peptides, have substantial bacterial activity against common pathogenic microorganisms and stimulate fibroblast and keratinocyte growth in vitro. These defensin-class peptides are compounds with potent antimicrobial activity that at the same concentration that is antimicrobially effective concurrently stimulate fibroblast and keratinocyte growth. Unlike many topical antibacterial agents that are inhibitive of cellular growth and wound healing, these defensin peptides can be usefully employed in the practice of the present invention to promote cellular growth and wound healing as topical antimicrobial agents following burn injury, as well as in post-surgical applications.

While the invention has been described herein, with respect to certain features, aspects, and embodiments, it will be recognized that the invention may be widely varied, and that numerous other modifications, variations, and other embodiments are possible, and that such modifications, variations, and other embodiments are to be regarded as being within the spirit and scope of the invention.

---

What is claimed is:

1. A method of promoting wound healing in a mammalian subject having a wound in need of treatment comprising administering to said subject a composition of a fibroblast and keratinocyte proliferatingly effective amount of an amphipathic peptide, wherein the amphipathic peptide comprises a peptide having a sequence selected from SEQ ID nos. 1 to 3, 5 to 38 and 40, wherein said wound is selected from the group consisting of thermal injury wounds and surgical wounds.

2. A method of stimulating the accelerated growth of dermal tissue in a tissue culture containing the same, comprising applying to the tissue culture a fibroblast and keratinocyte proliferatingly effective amount of an amphipathic peptide selected from the group consisting of SEQ ID Nos. 1 to 3, 5 to 38 and 40.

3. The method of claim 2 wherein the dermal tissue is grown to produce tissue for grafting onto a burn or surgical wound.

4. The method of claim 3 wherein the dermal tissue is tissue from a subject in need of a tissue graft.

* * * * *